(12) United States Patent
Tanii

(10) Patent No.: US 10,092,170 B2
(45) Date of Patent: Oct. 9, 2018

(54) INSERTION APPARATUS

(71) Applicant: OLYMPUS CORPORATION, Hachioji-shi, Tokyo (JP)

(72) Inventor: Yoshiyuki Tanii, Fussa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/254,922

(22) Filed: Sep. 1, 2016

(65) Prior Publication Data
US 2016/0367110 A1    Dec. 22, 2016

Related U.S. Application Data

(63) Continuation of application No. PCT/JP2015/073881, filed on Aug. 25, 2015.

(30) Foreign Application Priority Data

Aug. 29, 2014 (JP) .................................. 2014-176192

(51) Int. Cl.
| | |
|---|---|
| *A61B 1/04* | (2006.01) |
| *A61B 1/005* | (2006.01) |
| *A61B 1/00* | (2006.01) |
| *A61B 1/015* | (2006.01) |

(52) U.S. Cl.
CPC .......... *A61B 1/0051* (2013.01); *A61B 1/0008* (2013.01); *A61B 1/0011* (2013.01); *A61B 1/0014* (2013.01); *A61B 1/0055* (2013.01); *A61B 1/00128* (2013.01); *A61B 1/00135* (2013.01); *A61B 1/015* (2013.01)

(58) Field of Classification Search
CPC ............................ A61B 1/0008; A61B 1/0014
USPC .................................. 600/121–125, 127, 129
See application file for complete search history.

(56) References Cited

U.S. PATENT DOCUMENTS 4,296,955 A * 10/1981 Martin ................... F16B 1/0014
                                                                285/381.1
4,879,991 A * 11/1989 Ogiu ......................... A61B 1/05
                                                                600/110

(Continued)

FOREIGN PATENT DOCUMENTS

| JP | S59-197233 A | 11/1984 |
|---|---|---|
| JP | H10-192222 A | 7/1998 |

(Continued)

OTHER PUBLICATIONS

Nov. 17, 2015 International Search Report issued in International Patent Application No. PCT/JP2015/073881.

(Continued)

*Primary Examiner* — Matthew J Kasztejna
(74) *Attorney, Agent, or Firm* — Oliff PLC

(57) ABSTRACT

The insertion apparatus includes: a linearly-extending insertion section main body, an outer tube covering the outer circumference of the insertion section main body, and an annular band member provided on the outer tube in such a manner as to meander on an imaginary circle on the outer tube whose center is the same as the central axis of the insertion section main body. The annular band member is configured to shrink in the direction along the imaginary circle and thereby secure the outer tube to the insertion section main body.

15 Claims, 13 Drawing Sheets

(56) References Cited

U.S. PATENT DOCUMENTS

| | | | |
|---|---|---|---|
| 8,747,303 B2* | 6/2014 | Furuta | A61B 1/0008 156/187 |
| 8,920,311 B2* | 12/2014 | LaBombard | A61B 1/00087 600/104 |
| 2003/0069472 A1 | 4/2003 | Butler | |
| 2005/0049460 A1* | 3/2005 | Mikkaichi | A61B 1/00135 600/121 |
| 2007/0142709 A1 | 6/2007 | Martone et al. | |
| 2008/0228029 A1* | 9/2008 | Mikkaichi | A61B 1/00142 600/104 |
| 2008/0249362 A1 | 10/2008 | Jiang et al. | |
| 2009/0093680 A1* | 4/2009 | Tsutsumi | A61B 1/0008 600/140 |
| 2010/0125164 A1* | 5/2010 | LaBombard | A61B 1/00087 600/104 |
| 2012/0215068 A1* | 8/2012 | Furuta | A61B 1/0008 600/125 |

FOREIGN PATENT DOCUMENTS

| | | |
|---|---|---|
| JP | 3869509 B2 | 1/2007 |
| JP | 2009-195456 A | 9/2009 |
| WO | 2011/052303 A1 | 5/2011 |

OTHER PUBLICATIONS

Mar. 9, 2017 Transmittal of Translation of IPRP issued in International Application No. PCT/JP2015/073881.

Apr. 17, 2018 Extended European Search Report issued in European Patent Application No. 15836455.4.

\* cited by examiner

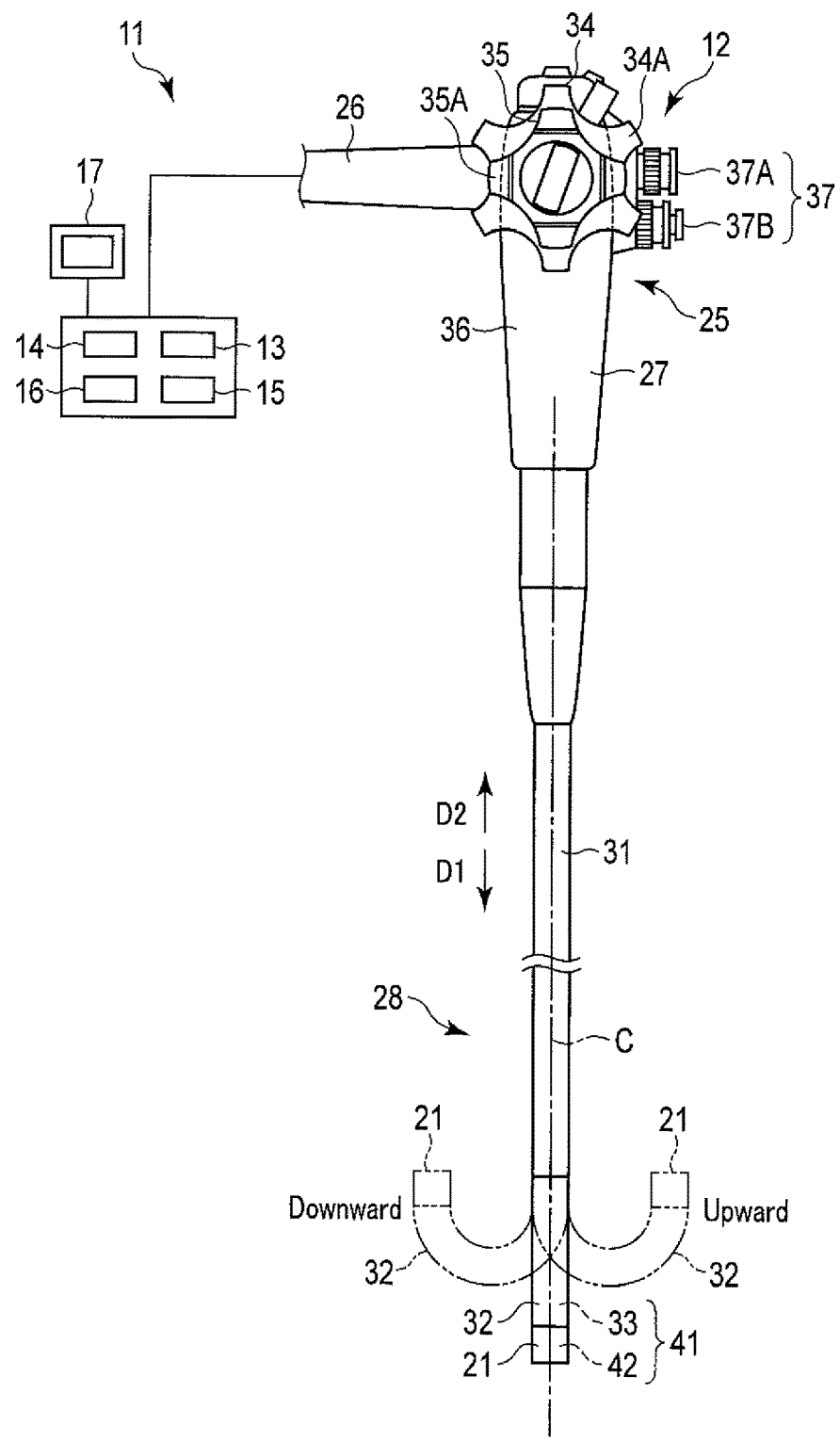
F I G. 1

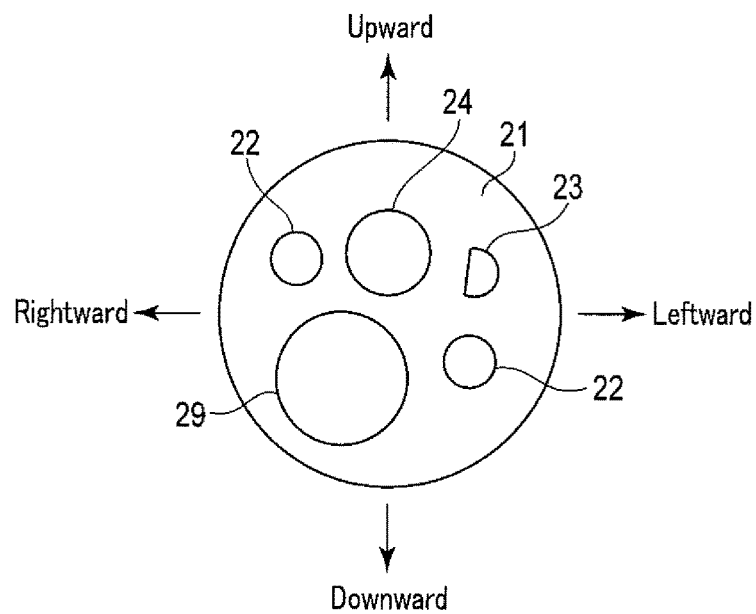
F I G. 2
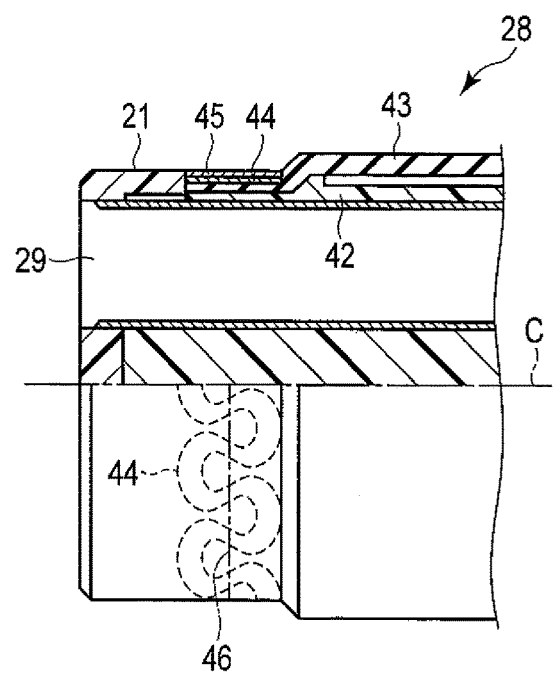
F I G. 3

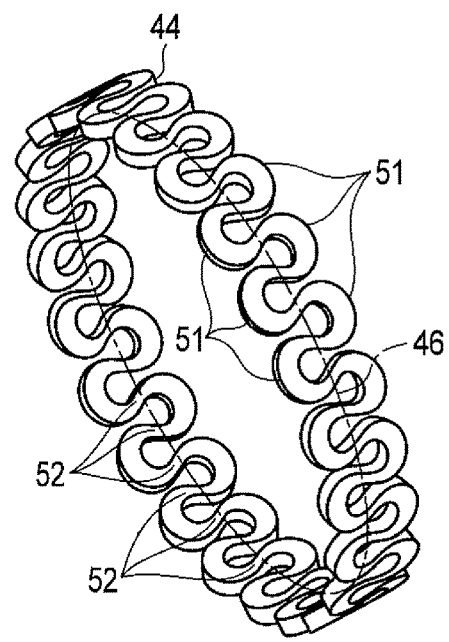
F I G. 4
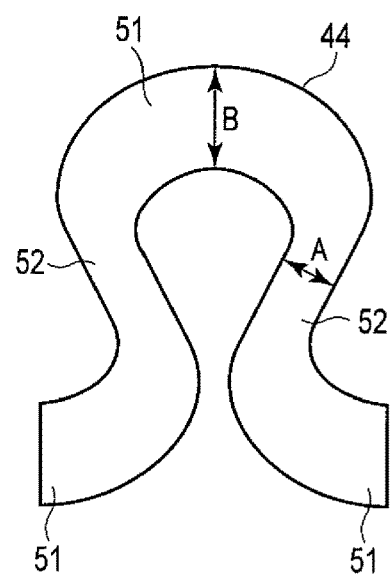
F I G. 5

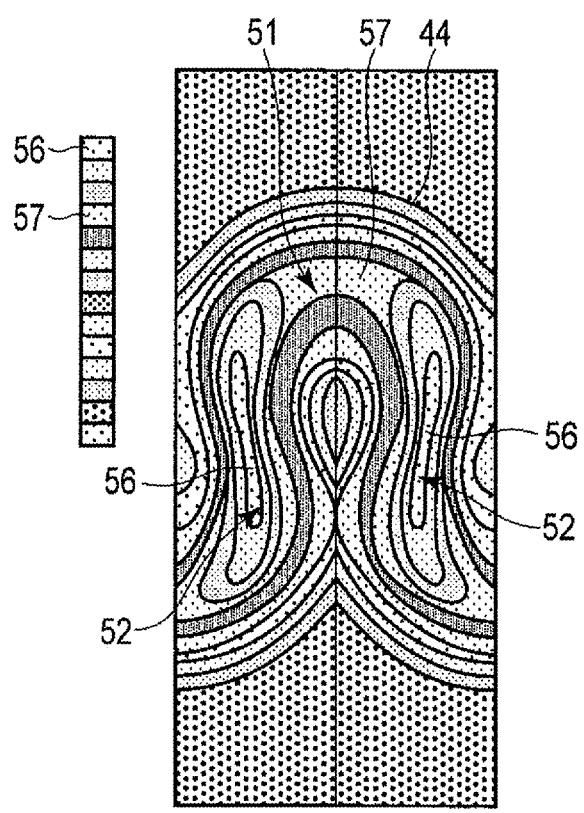
F I G. 8

INSERTION APPARATUS

CROSS-REFERENCE TO RELATED APPLICATIONS

This application is a Continuation Application of PCT Application No. PCT/JP2015/073881, filed Aug. 25, 2015 and based upon and claiming the benefit of priority from prior Japanese Patent Application No. 2014-176192, filed Aug. 29, 2014, the entire contents of all of which are incorporated herein by reference.

BACKGROUND OF THE INVENTION

1. Field of the Invention

The present invention relates to an insertion apparatus to be inserted into a cavity.

2. Description of the Related Art

In general, an insertion apparatus to be inserted into a cavity, such as an endoscope, comprises a flexible insertion section which is to be inserted into an examinee for observation and treatment of an affected portion of the examinee, and an operation section which is operated to bend the insertion section in a UD direction and an RL direction. The operation section is provided with a bending operation knob. When the affected portion is observed or treated, the bending portion at the distal end of the insertion section can be curved in a desired direction by operating the bending operation knob.

An outer tube, covering the bending portion of the insertion section of the endoscope, can be secured by means of a string or a shape memory alloy.

Prior Art Document

Patent Literature

[Patent Document 1] Jpn. Pat. Appln. KOKAI Publication No. 59-197233

SUMMARY OF THE INVENTION

Object of the Invention

When the string is used for securing the outer tube, it is difficult to wind the string with a uniform force. Nor is it difficult to determine a winding start position and a winding end position. The winding operation may be performed differently depending upon operator, and is generally time-consuming and requires skill on the part of the operator. The terminating end of the string is tied in such a manner as not to unfasten. In this case, the knot of the string is inevitably thick and may degrade the smoothness of the outer surface. On the other hand, when the shape memory alloy is used for securing the outer tube, it is first expanded and made to cover the outer tube and is then heated for restoration. In this case, the outer tube must not be melted by the heat in the heat treatment. In addition, the shape memory alloy must not be shifted relative to the outer tube, and stress should be uniformly generated throughout the circumferential direction of the outer tube. As a result, the manufacturing process may be complicated. In the case of Patent Document 1, a cylindrical shape memory alloy is used, and this type of shape memory alloy cannot be easily expanded when it is attached to an outer tube.

Means for Achieving the Object

The insertion apparatus comprises an insertion section to be inserted into an examinee; a covering configured to cover the outer circumference of the insertion section; and an annular band member provided on the outer circumference of the covering in such a manner as to meander on an imaginary circle on the covering whose center is the same as the central axis of the insertion section, the annular band member being configured to shrink in the direction along the imaginary circle and thereby secure the covering to the insertion section.

Advantages of the Invention

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view showing the entire structure of an endoscope apparatus according to the first embodiment.

FIG. 2 is a front view showing how the distal-end hard portion of the endoscope apparatus looks like when viewed from the end face.

FIG. 3 is a longitudinal section of the distal-end hard portion depicted in FIG. 2.

FIG. 4 is a perspective view showing a band member used for the insertion section of the endoscope apparatus depicted in FIG. 1, FIG. 5 is a front view showing part of the band member depicted in FIG. 4 in an enlarged scale.

FIG. 8 illustrates how a pressing force is distributed in part of the band member of the comparative example.

DESCRIPTION OF EMBODIMENTS

First Embodiment

Figure 6:
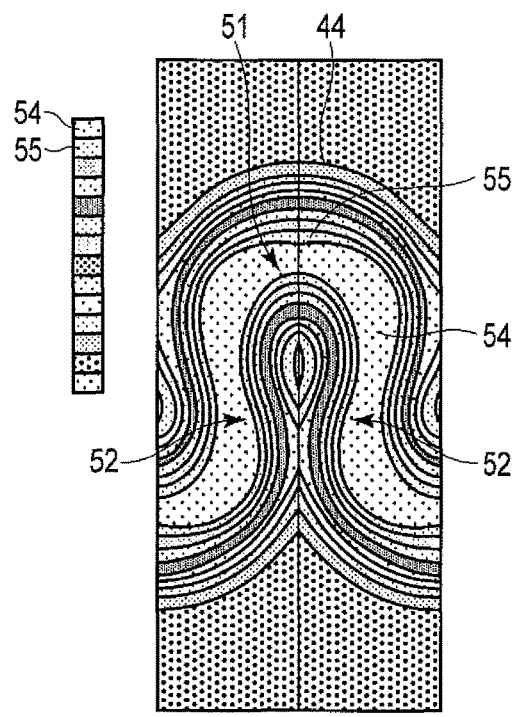
FIG. 6 illustrates how a pressing force is distributed in part of the band member depicted in FIG. 5.

An endoscope apparatus according to the fifth embodiment will be described with reference to FIGS. 1 to 10. FIG. 1 shows the entire structure of an endoscope apparatus according to the present invention. As shown in FIG. 1, the endoscope apparatus 11 comprises an endoscope 12, a controller 13 which performs control including image processing, a light source 14, an air supply/water supply/suction apparatus 15, a keyboard 16 and a monitor 17.

Under the control of the controller 13, the light source 14 supplies light to an illumination lens 22, located at the distal-end hard portion 21 (mentioned later) of the endoscope 12. In response to an operation of a button section 37 provided on the operation section (to be described later), the air supply/water supply/suction apparatus 15 supplies air or water to the nozzle 23 of the distal-end hard portion 21 of the endoscope 12, or sucks a liquid or a tissue from within a living body through a treatment tool insertion channel 29. The image processor of the controller 13 performs image processing for an image signal of the examinee captured with an objective lens 24 of the distal-end hard portion 21 of the endoscope 12, and displays an image on the monitor 17.

As shown in FIG. 1, the endoscope 12 comprises an operation section 25, a universal code 26 for coupling the operation section 25 and the controller 13, a grip 27 adjacent to the operation section 25, and an insertion section 28 extending from the grip 27 and configured to be inserted into a cavity (examinee). The endoscope 12 is an example of the insertion apparatus. The endoscope 12 is connected to the controller 13, light source 14, and air supply/water supply/suction apparatus 15 by means of the universal code 26.

In FIG. 1, arrow D1 indicates the direction toward the longitudinal distal end, and arrow D2 indicates the direction toward the longitudinal proximal end. The insertion section 28 includes a flexible tube portion 31 which is elongated and flexible, a bending portion 32 located at the distal end of the flexible tube portion, and a distal-end hard portion 21 located at the distal end of the bending portion 32.

The bending portion 32 contains a plurality of cylindrical bending pieces 33 arranged along the longitudinal axis C of the insertion section 28. A pin is interposed between the adjacent bending pieces 33 to enable the being pieces 33 to change their angles. The bending pieces 33 form a joint enabling the bending portion 32 to bend. The outer circumference of the bending portion 32 is covered with an outer tube (described later). A pair of first wires for enabling the bending portion 32 to bend in a U direction or in a D direction opposite thereto, and a pair of second wires for enabling the bending portion to bend in an R direction or in an L direction opposite thereto, are inserted through the bending pieces 33. The first wires and the second wires are fixed to the bending piece 33 located at the most distal end of the insertion section 33. In the operation section 25, the paired first wires are fixed to a first pulley of a first dial unit 34. Likewise, in the operation section 25, the paired second wires are fixed to a second pulley of a second dial unit 35. The bending pieces 33, first wires and second wires enable the bending portion 32 to bend in the U direction, D direction, R direction, L direction, or any direction obtained by combining these directions.

As shown in FIG. 2, the distal-end hard portion 21 is provided with an objective lens 24, a treatment tool insertion channel 29 used for sucking a liquid and a tissue from within a living body and for treating an affected portion, an illumination lens 22, and a nozzle 23 for supplying cleaning water or air to the objective lens 24.

As shown in FIG. 1, the operation section 25 comprises a case 36 made, for example, of a synthetic resin, a first dial unit 34 projected from the case 36 and rotatable relative to the case 36, a second dial unit 35 projected from the case 36 and rotatable relative to the case 36, and a button section 37 provided for the case 36. The button section 37 includes a first button 37A (an air supply/water supply button) operated when air or water is supplied to the distal-end hard portion 21 of the endoscope 12 through the nozzle 23, and a second button 37B (a suction button) operated when the distal-end hard portion 21 of the endoscope 12 performs suction through the treatment tool insertion channel 29.

The first dial unit 34 is operated when the bending portion 32 should be bent in the U direction (upward) or the D direction (downward). When the user operates the UD knob 34A of the first dial unit 34, the first pulley is rotated, pulling one of the first wires and releasing the tension of the other first wire. As a result, the bending portion 32 is bent in the U direction or the D direction.

The second dial unit 35 is operated when the bending portion 32 should be bent in the R direction (rightward) or the L direction (leftward). When the user operates the RL knob 35A of the second dial unit 35, the second pulley is rotated, pulling one of the second wires and releasing the tension of the other second wire. As a result, the bending portion 32 is bent in the R direction or the L direction.

A detained description will be given of the structure of the insertion section 28 with reference to FIG. 3. The insertion section 28 includes an insertion section main body 41 provided inside thereof and extending linearly. The insertion section main body 41 includes the internal structure of the flexible tube portion 31, and a plurality of bending pieces 33 which constitute the internal structure of the bending portion, and a cylindrical internal block 42 (the distal-end hard portion 21) which constitutes the internal structure of the distal-end hard portion 21. The distal-end hard portion 21 is formed, for example, of a synthetic resin or metal and is fixed to the bending piece 33 located at the most distal end. The insertion section 28 comprises a cylindrical outer tube 43 (formed of rubber or a rubber-like elastic material) covering the insertion section main body 41 formed as above, an annular band member 44 covering the outer tube 43 and securing the outer tube 43 to the insertion section main body 41, and an adhesive layer 45 covering the outer surface of the band member 44. If required, a second adhesive layer may be provided between the distal-end hard portion 21 and the outer tube 43 by coating an adhesive.

The outer tube 43 is formed, for example, of a rubber material. The adhesive layer 45 is formed, for example, by coating an epoxy adhesive on the outer surface of the band member 44 in the state where the band member 44 secures the outer tube 43.

As shown in FIG. 3, the band member 44 is provided in such a manner as to meander on an imaginary circle 46 on the outer tube 43 whose center is the same as the central axis C of the insertion section main body 41. The band member 44 can be regarded as a repeated pattern of the letter "S". The band member 44 is expansible and contractible in the direction along the imaginary circle 46. Before being expanded, the band member 44 has a diameter φE smaller than that of the diameter φG of the outer tube 43. After being expanded, the band member 44 has a diameter φF larger than that of the diameter φG of the outer tube 43 (see FIG. 9). The expansion of the band member 44 from φE to φF can be controlled in a so-called elastic deformation region. Part of the expansion from φE to φF may be controlled in a plastic deformation region.

The band member 44 can fix the outer tube 43 to the distal-end hard portion 21 in a watertight manner. The band member 44 is made of a metallic material. To be more specific, the band member 44 is formed of a titanium-based alloy, such as Ni—Ti alloy. Because of the property of the titanium-based alloy, the band member 44 can provide superelasticity. Being superelastic, the band member 44 can exhibit elasticity like that of rubber. In the state where the band member 44 covers the outer surface of the outer tube 43, the band member 44 provides a watertight structure between the distal-end hard portion 21 and the outer tube 43. In addition, the band member 44 provides such a tightening force as prevents the outer tube 43 from slipping off the distal-end hard portion 21.

As shown in FIG. 4, the band member 44 includes a plurality of arch portions 51 and a plurality of connection portions 52 connecting the arch portions 51. The adjacent arch portions 51 are directed in opposite directions. As shown in FIG. 3, the arch portions 51 are arranged on the imaginary circle 46 on the outer tube 43 whose center is the same as the central axis C of the insertion section main body 41. Each of the arch portions 51 overlaps the adjacent arch portions 51 in the direction along the imaginary circle 46. The central axis C of the insertion section main body 41 is the same as the longitudinal axis C of the insertion section 28.

The connection portions 52 extend in directions intersecting with the imaginary circle 46. As shown in FIG. 5, dimension A of the connection portion 52, which is the widthwise dimension of the connection portion 52 (i.e., the dimension as measured in the transverse direction of the connection portion 52), is equal to or less than dimension B of the arch portion 51, which is the widthwise dimension of the arch portion 51 (i.e., the dimension as measured in the transverse direction of the arch portion 51). That is, A≤B. It should be noted that the widthwise direction is intended to mean the direction orthogonal to the central axis of the band member 44 made up of the arch portions 51 and connection portions 52.

A description will be given of the waterproof effect of the band member 44 of the present embodiment, with reference to FIG. 6. FIG. 6 illustrates how the pressure is distributed in the band member 44. For example, regions 54 and 55 have a pressure not less than 10.13 kPa, the water pressure at a depth of 1 m, and therefore satisfies the waterproof standard of JIS. To be more specific, the pressure in region 54 is a pressing force of 15 to 18 kPa, and the pressure in region 55 is a pressing force of 12 to 15 kPa. In this manner, sufficient waterproof property (watertightness) is ensured in regions 54 and 55.

Figure 7:
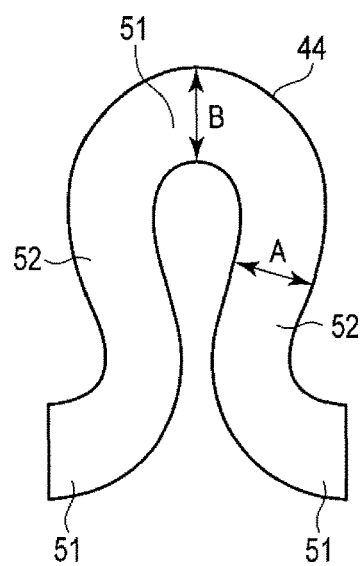
FIG. 7 is a front view showing part of a band member according to a comparative example.

A description will be given of a band member 44 according to a comparative example with reference to FIG. 7 and FIG. 8. In the band member 44 of the comparative example, dimension A of connection portion 52, which is the dimension of connection portion 52 as measured in the transverse direction, is equal to dimension B of arch portion 51, which is the dimension arch portion 51 as measured in the transverse direction. That is, A=B. In the band member 44 of the comparative example, stress is concentrated in connection portion 52 when the band member 44 is fitted on the outer tube 43. As a result, when the band member 44 of the comparative example is fitted on the outer tube 43, the pressure with which the outer tube 43 is pushed tends to decrease in arch portions 51. To be specific, the pressing force in region 56 corresponding to connection portion 52 is 18 to 21 kPa, while the pressing force in region 57 corresponding to arch portion 51 is 9 to 12 kPa. Therefore, the band member 44 of the comparative example does not satisfy the proof standard of JIS in arch portions 51. In region 57, therefore, the pushing force should be at least 10.13 kPa (e.g., 12 kPa or more).

Figure 9:
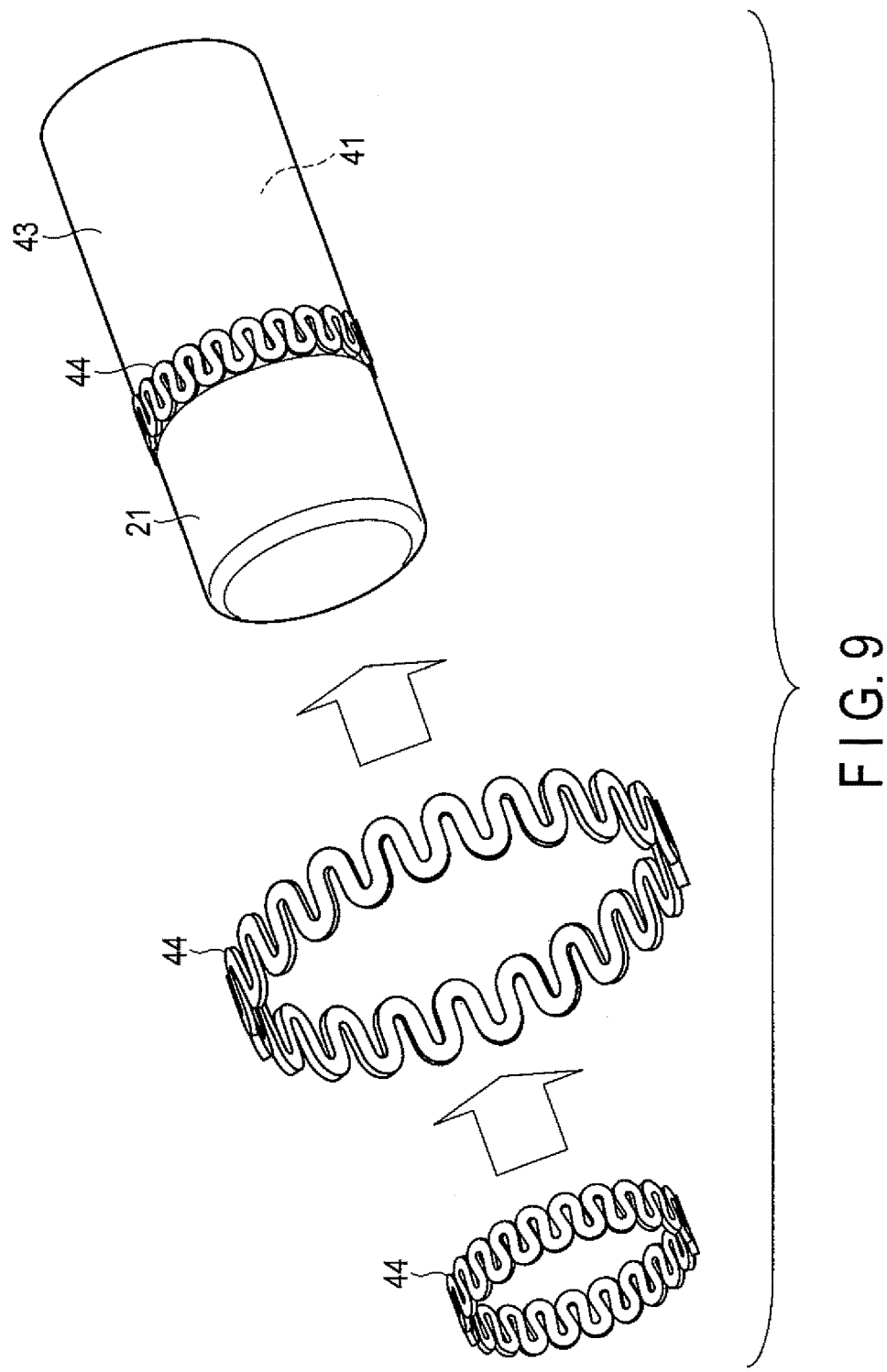
FIG. 9 is a perspective view illustrating a step in which the band member depicted in FIG. 4 is made to cover the covering.

A description will be given of the manufacturing process of the insertion section 28 of the present embodiment with reference to FIG. 9. The insertion section main body 41 is covered with an outer tube 43 beforehand. A second adhesive layer is provided at the position where the insertion section main body 41 and the outer tube 43 are fixed to each other. The second adhesive layer helps fix the insertion section main body 41 and the outer tube 43 to each other. The band member 44 is expanded to increase the diameter manually or by using a jig. In this expanded state, the band member 44 is fitted around the outer tube 43, and the outer tube 43 is fixed to the insertion section main body 41 by the band member 44. Then, an adhesive is coated over the band member 44, thereby forming an adhesive layer 45. In this manner, the outer tube 43 is fixed to the insertion section main body 41.

Figure 10:
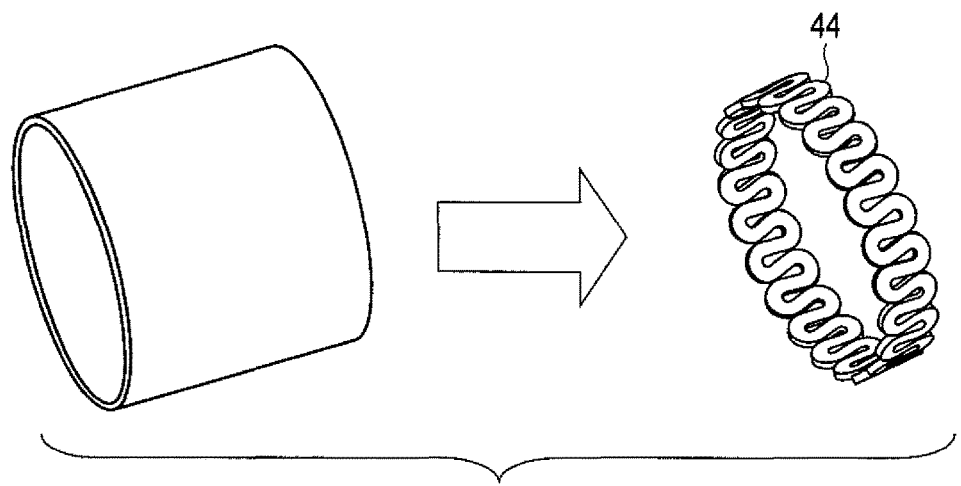
FIG. 10 is a perspective view illustrating a process in which the band member of the first embodiment is manufactured.

As shown in FIG. 10, according to the first embodiment, the band member 44 is formed by cutting a cylindrical tube to obtain an annular band member by laser beam machining.

According to the first embodiment, the insertion apparatus comprises: a linearly-extending insertion section main body 41; a cylindrical outer tube 43 covering the outer circumference of the insertion section main body 41; and an annular band member 44 provided on the outer tube 43 in such a manner as to meander on an imaginary circle 46 on the outer tube 43 whose center is the same as the central axis of the insertion section main body 41, the annular band member being configured to expand or shrink in the direction along the imaginary circle and thereby secure the outer tube 43 to the insertion section main body 41.

With this structure, the annular band member 44 is expanded and fitted around the outer tube 43. By so doing, the annular band member 44 can be easily secured to the insertion section main body 41 by a one-touch operation. Accordingly, an operator who secures the outer tube 43 does not require skill, and the assembling operation of the insertion apparatus can be simplified. As a result, the assembling time can be shortened. Unlike the case where the outer tube 43 is fixed by means of a string, the tightening force (fastening force) is prevented from being non-uniform.

The band member 44 includes a plurality of arch portions 51 extending in the direction along the imaginary circle 46 and a plurality of connection portions 52 connecting the arch portions 51. With this structure, the band member 44 is expansible/contractible and yet simple in shape.

The dimension of arch portions 51 as measured in the transverse direction is larger than the dimension of connection portions 52 as measured in the transverse direction.

With this structure, when the outer tube 43 is secured to the insertion section main body 41 by means of the band member 44, uniform pressure distribution is attained in those portions of the outer tube 43 which are located beneath the band member 44. Accordingly, watertightness is provided between the insertion main body 41 and the outer tube 43, enhancing the reliability of the insertion apparatus.

Each of the arch portions 51 overlaps the adjacent arch portions 51 in the direction along the imaginary circle 46. With this structure, the band member 44 allows room for expansion in the direction along the imaginary circle 46. Accordingly, the insertion apparatus can be assembled efficiently.

The band member 44 has a diameter smaller than that of the outer tube 43, and can be expanded to have a diameter larger than that of the outer tube 43 when it is fitted around the outer tube 43. With this structure, when the band member 44 is used for securing the outer tube 43, it is expanded and fitted around the outer tube 43. Thereafter, the band member 44 is released from the expanded state. Accordingly, the operation of securing the outer tube 43, which required skill in the conventional art, can be performed easily and in a short time. The band member 44 is formed of a metal having superelasticity. With this structure, the band member 44 is kept from breaking when the band member 44 is expanded and secured to the outer tube 43.

(First Modification)

Figure 11:
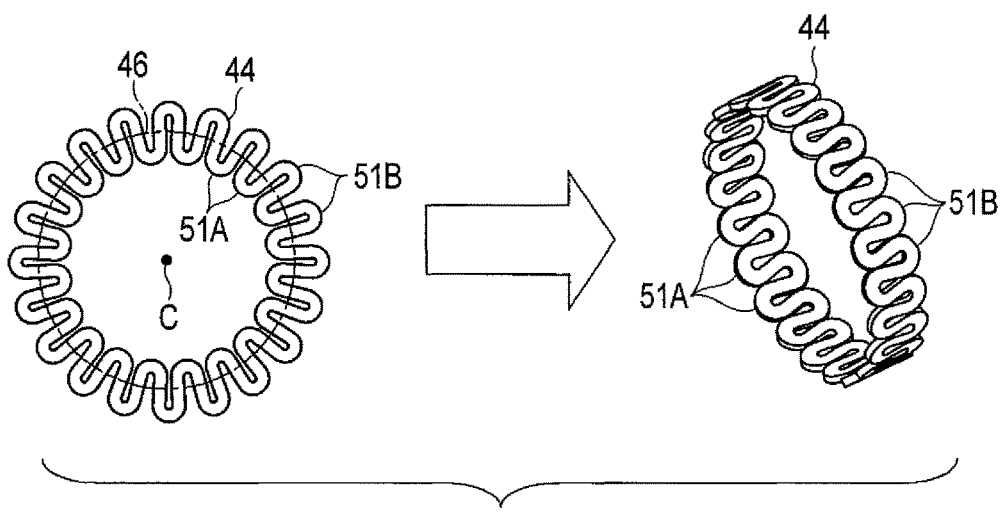
FIG. 11 is a perspective view illustrating a band member according to the first modification of the first embodiment.

A description will be given of a band member 44 according to the first modification, with reference to FIG. 11. According to the first modification, the band member 44 is formed by cutting a flat metallic plate into a star or flower shape by laser beam machining. The flat metallic plate is formed of such a titanium-based alloy as a Ni—Ti alloy. The band member 44 obtained after cutting is in a single flat plane. The band member 44 includes a plurality of arch portions 51 extending in the direction along an imaginary circle 46 and a plurality of connection portions 52 connecting the arch portions 51.

The arch portions 51 include center-side arch portions 51A located closer to the central axis C than the imaginary circle 46, and outer-side arch portions 51B located outward of the imaginary circle 46. The dimension of the outer-side arch portions 51B, as measured along the imaginary circle 46, is greater than the dimension of the center-side arch portions 51A, as measured along the imaginary circle 46.

The band member 44 having this shape is changed into a cylindrical tube by means of a jig. In this state, the band member 44 is subjected to heat treatment, by which the internal stress is removed from the band member 44. In these steps, the cylindrical band member 44 can be formed. The band member 44 of the first modification is free of internal stress as a result of the heat treatment and can be expanded or contracted smoothly. In addition, the band member 44 free of internal stress enables the outer tube 43 to be pressed uniformly by the band member 44, without reference to the portions of the band member 44.

(Second Modification)

A description will be given of a band member 44 according to the second modification. According to the second modification, the band member 44 is formed by cutting a flat metallic plate into a star or flower shape by laser beam machining, as in the first modification. The flat metallic plate is formed of such a titanium-based alloy as a Ni—Ti alloy. The shape of the ring member obtained immediately after cutting is similar to the band member of the first modification depicted in FIG. 11, and is in a single flat plane. According to the second modification, the band member 44 is not subjected to heat treatment. When the band member 44 formed in two dimensions is fitted around the outer tube 43, it falls along the circumferential surface of the outer tube 43. Since the radius of the outer tube 43 covering the insertion section main body 41 is greater than the radius of the band member 44, the internal portions of the band member 44 (namely, the center-side arch portions 51A) are opened. Because of the superelastic characteristics of the Ni—Ti alloy, the outer portions of the band member 44 (namely, the outer-side arch portions 51B) contract in response to the opening of the inner portions of the band member 44 (namely, the center-side arch portions 51A). The band member 44 is secured to the outer tube 43 in the state where the contraction force of the inner portions of the band member (namely, the center-side arch portions 51B) is in balance with the expansion force of the outer portions of the band member 44 (namely, the outer-side arch portions 51B). Based on this principle, the band member 44 does not have to be subjected to any heat treatment, and yet enables the outer tube 43 to be pressed uniformly.

According to the second modification, the band member is formed from one flat plane, and yet it can be changed into a cylindrical member when it is fitted around the outer tube 43. With this structure, the band member 44 can be formed from one sheet-like material, and the manufacturing cost of such a band member is low.

The arch portions 51 include center-side arch portions 51A located closer to the central axis C than the imaginary circle 46, and outer-side arch portions 51B located outward of the imaginary circle 46. The dimension of the outer-side arch portions, as measured along the direction of the imaginary circle 46, is greater than the dimension of the center-side arch portions 51A, as measured along the imaginary circle 46. With this structure, the band member 44 can be made from one sheet-like material. Accordingly, the working step for cutting out the band member 44 can be as simple as possible, and the manufacturing cost can be reduced, accordingly.

(Third Modification)

Figure 12:
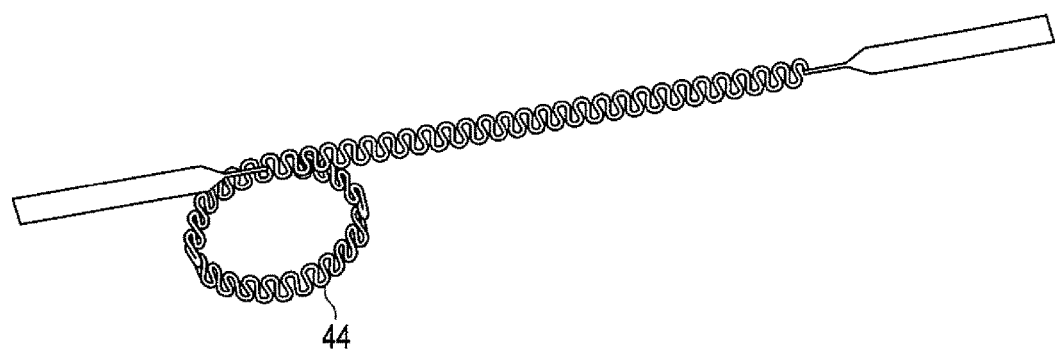
FIG. 12 is a perspective view illustrating a band member according to the third modification of the first embodiment.

A description will be given of a band member 44 according to the third modification, with reference to FIG. 12. According to the third modification, the band member 44 is formed by cutting a flat metallic plate into a band having a repeated shape of the letter "S" by laser beam machining. The flat metallic plate is formed of such a titanium-based alloy as a Ni—Ti alloy. The band is cut to have a proper length, and the ends are joined by welding, thereby forming an annular (cylindrical) band member 44. The band member 44 thus obtained has advantages similar to those of the first embodiment, first modification and second modification.

Second Embodiment

Figure 13:
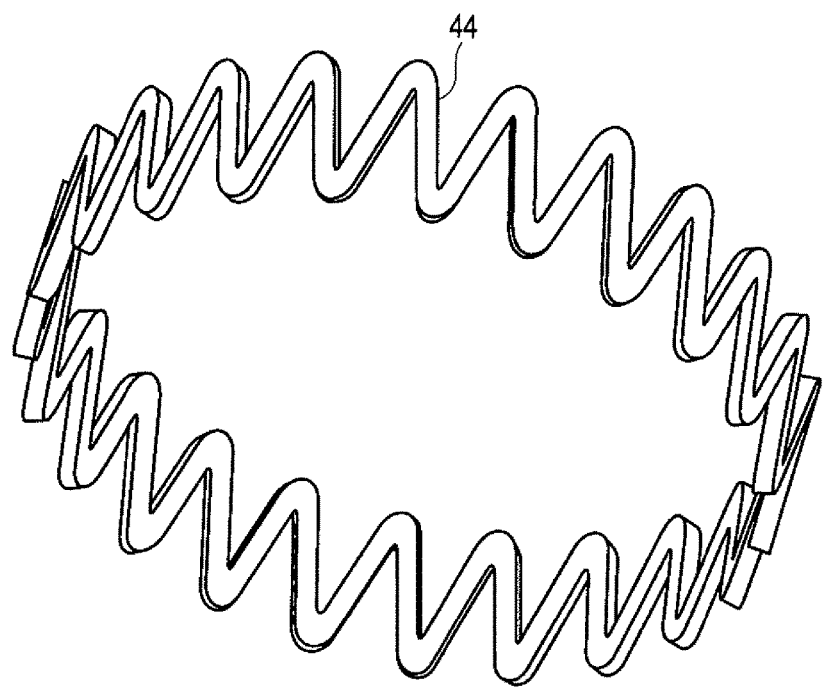
FIG. 13 is a perspective view showing a band member used for the insertion section of an endoscope apparatus according to the second embodiment.
Figure 14:
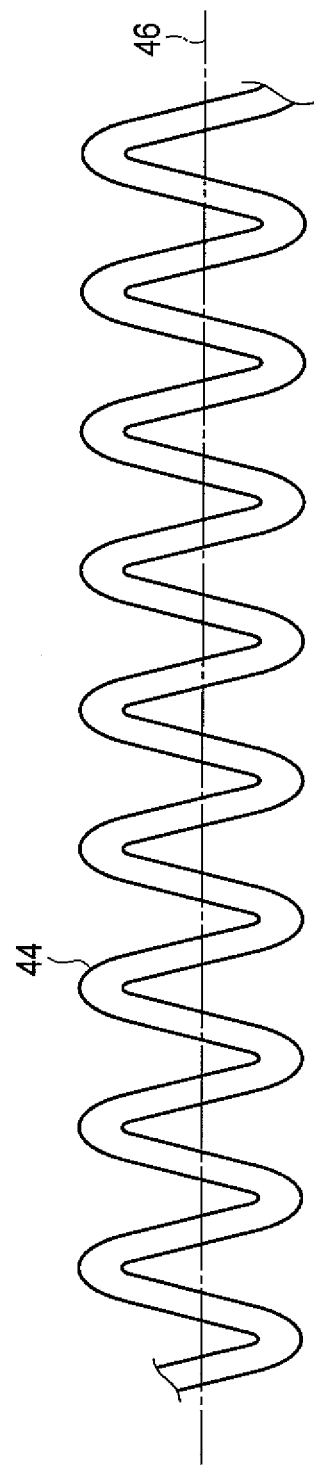
FIG. 14 is a front view showing part of the band member depicted in FIG. 13 in an enlarged scale.

An endoscope apparatus according to the second embodiment will be described with reference to FIGS. 13 and 14. The band member 44 of the endoscope apparatus 11 of the second embodiment differs from that of the first embodiment in that it has a sine curve, but the other features are similar to those of the first embodiment. A description will therefore be given mainly of how the second embodiment differs from the first embodiment. As for the features common to the first embodiment, a description and illustration of them will be omitted.

The band member 44 is provided annually in such a manner as to meander on an imaginary circle 46 on the outer tube 43 whose center is the same as the central axis C of the insertion section main body 41. The band member 44 can fix the outer tube 43 to the distal-end hard portion 21 in a watertight manner. The band member 44 is formed of such a titanium-based alloy as a Ni—Ti alloy. Because of the property of the titanium-based alloy, the band member 44 can provide superelasticity. Being superelastic, the band member 44 can exhibit elasticity like that of rubber.

According to the second embodiment, the band member 44 forms a sine curve. With this structure, the band member 44 of the second embodiment may be somewhat inferior to the band member 44 of the first embodiment in terms of the expansion and contraction characteristics, but like the band member 44 of the first embodiment, the band member 44 of the second embodiment ensures reliable watertightness between the insertion section main body 41 and the outer tube 43.

Third Embodiment

Figure 15:
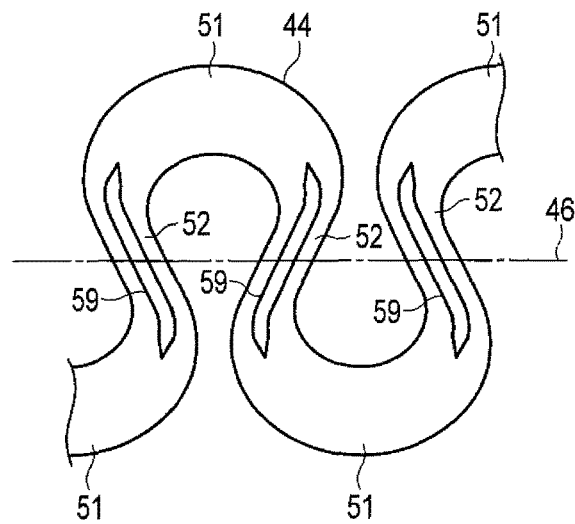
FIG. 15 is a front view showing part of a band member used for the insertion section of an endoscope apparatus according to the third embodiment.

An endoscope apparatus according to the third embodiment will be described with reference to FIG. 15. The band member 44 of the endoscope apparatus 11 of the third embodiment differs from that of the first embodiment in that it has slits 59, but the other features are similar to those of the first embodiment. A description will therefore be given mainly of how the third embodiment differs from the first embodiment. As for the features common to the first embodiment, a description and illustration of them will be omitted.

The band member 44 is provided annually on the outer tube 43 in such a manner as to meander on an imaginary circle 46 on the outer tube 43 whose center is the same as the central axis C of the insertion section main body 41. The band member 44 can be regarded as a repeated pattern of the letter "S". The band member 44 can fix the outer tube 43 to the distal-end hard portion 21 in a watertight manner. The band member 44 is formed of such a titanium-based alloy as a Ni—Ti alloy. Because of the property of the titanium-based alloy, the band member 44 can provide superelasticity. Being superelastic, the band member 44 can exhibit elasticity like that of rubber.

The band member 44 includes a plurality of arch portions 51 and a plurality of connection portions 52 connecting the arch portions 51. The arch portions 51 are arranged on the imaginary circle 46 on the outer tube 43 whose center is the same as the central axis C. The connection portions 52 extend in directions intersecting with the imaginary circle 46. The slits 59 are formed to extend in the directions in which the connection portions 52 extend, and are provided throughout the whole length of the connection portions 52. The ends of the slits are acute. In a cross section of each connection portion 52, therefore, the percentage of the slit 59 gradually increases from the ends to the middle portion.

In the third embodiment, the cross sectional area of each connection portion 52 in the transverse direction thereof can be as small as possible, and stress is prevented from concentrating in the connection portions 52.

Fourth Embodiment

Figure 16:
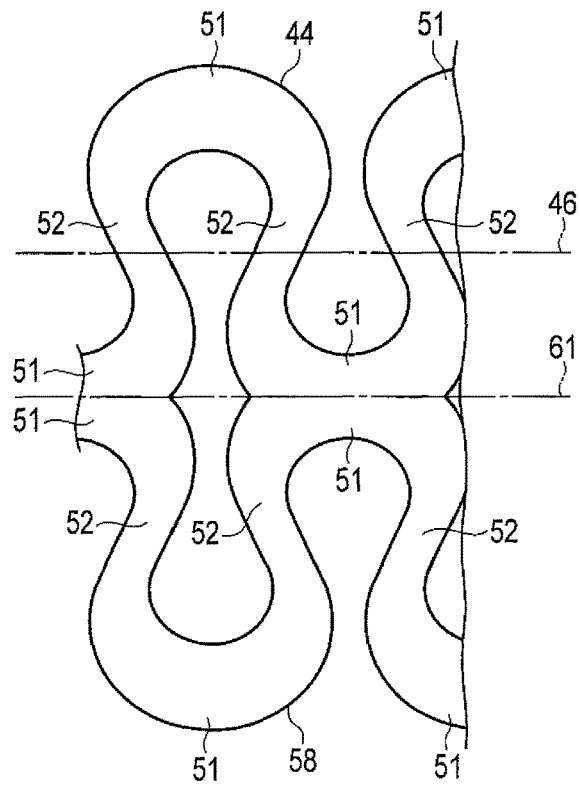
FIG. 16 is a front view showing part of a band member used for the insertion section of an endoscope apparatus according to the fourth embodiment.

An endoscope apparatus 11 according to the fourth embodiment will be described with reference to FIG. 16. The endoscope apparatus 11 of the fourth embodiment differs from that of the first embodiment in that it comprises a band member 44 and a second band member 58 integral with the band member 44, but the other features are similar to those of the first embodiment. A description will therefore be given mainly of how the fourth embodiment differs from the first embodiment. As for the features common to the first embodiment, a description and illustration of them will be omitted.

The band member 44 is provided annually on the outer tube 43 in such a manner as to meander on an imaginary circle 46 on the outer tube 43 whose center is the same as the central axis C of the insertion section main body 41. The second band member 58 is symmetric with the band member 44 with respect to a reference line 61 parallel to the imaginary circle 46. The second band member 58 is integral with the band member 44 at the positions of the reference line 61.

The band member 44 and the second band member 58 can fix the outer tube 43 to the distal-end hard portion 21 in a watertight manner. The band member 44 and the second band member 58 are formed of such a titanium-based alloy as a Ni—Ti alloy. Because of the property of the titanium-based alloy, the band member 44 and the second band member 58 can provide superelasticity. Being superelastic, the band member 44 and the second band member 58 can exhibit elasticity like that of rubber.

Each of the band member 44 and second band member 58 includes a plurality of arch portions 51 and a plurality of connection portions 52 connecting the arch portions 51. The arch portions 51 are arranged on the imaginary circle 46 on the outer tube 43 whose center is the same as the central axis C. Each of the arch portions 51 overlaps the adjacent arch portions 51 in the direction along the imaginary circle 46. The connection portions 52 extend in directions intersecting with the imaginary circle 46. As shown in FIG. 5, dimension A of connection portion 52 (i.e., the dimension as measured in the transverse direction of the connection portion 52) is equal to or less than dimension B of the arch portion 51 (i.e., the dimension as measured in the transverse direction of the arch portion 51). That is, A≤B.

According to the fourth embodiment, the insertion apparatus comprises a second band member 58 which is symmetric with the band member 44 with respect to the reference line 61 parallel to the imaginary circle 46 and which is integral with the band member 44. With this structure, the band member 44 and the second band member 58 provide watertightness between the insertion main body 41 and the outer tube 43, further enhancing the reliability of the insertion apparatus.

Fifth Embodiment

Figure 17:
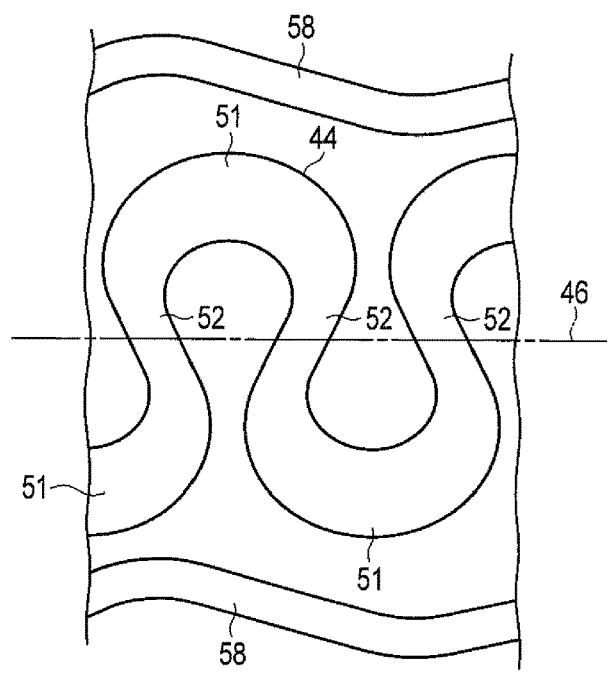
FIG. 17 is a front view showing part of a band member used for the insertion section of an endoscope apparatus according to the fifth embodiment.

An endoscope apparatus 11 according to the fifth embodiment will be described with reference to FIG. 17. The endoscope apparatus 11 of the fifth embodiment differs from that of the first embodiment in that it comprises a band member 44 and second band members 58 separate from the band member 44, but the other features are similar to those mentioned in connection with the first embodiment. A description will therefore be given mainly of how the fifth embodiment differs from the first embodiment. As for the features common to the first embodiment, a description and illustration of them will be omitted.

The band member 44 is provided annually on the outer tube 43 in such a manner as to meander on an imaginary circle 46 on the outer tube 43 whose center is the same as the central axis C of the insertion section main body 41. The band member 44 includes a plurality of arch portions 51 and a plurality of connection portions 52 connecting the arch portions 51. The other structural features of the band member 44 are similar to the features mentioned in connection with the first embodiment.

Each of the second band members 58 is provided annually on the outer tube 43 in such a manner as to meander on the imaginary circle 46, but the pitch of the meandering shape of the second band members 58 is different from that of the band member 44. The second band members 58 are provided in pairs, and the band member 44 is located between the second band members 58. The curvature factor of the second band members 58 is less than that of the band member 44. The meandering width of the second band members 58 is less than that of the band member 44.

The band member 44 and the second band members 58 can fix the outer tube 43 to the distal-end hard portion 21 in a watertight manner. The band member 44 and the second band members 58 are formed of such a titanium-based alloy as a Ni—Ti alloy. Because of the property of the titanium-based alloy, the band member 44 and the second band members 58 can provide superelasticity. Being superelastic, the band member 44 and the second band members 58 can exhibit elasticity like that of rubber.

According to the fifth embodiment, the insertion apparatus comprises annular second band members 58 which meander on the imaginary circle 46 at a pitch different from that of the band member 44. With this structure, not only the band member 44 but also the second band members 58 provides watertightness between the insertion main body 41 and the outer tube 43, enhancing the reliability of the insertion apparatus.

Sixth Embodiment

Figure 18:
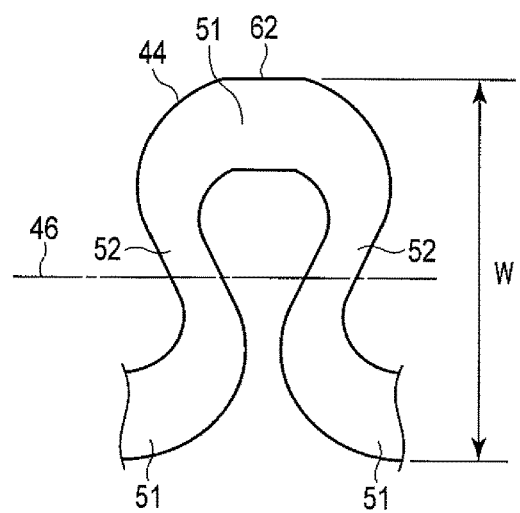
FIG. 18 is a front view showing part of a band member used for the insertion section of an endoscope apparatus according to the sixth embodiment.

An endoscope apparatus 11 according to the sixth embodiment will be described with reference to FIG. 18. The endoscope apparatus 11 of the sixth embodiment differs from that of the first embodiment in that the shape of the band member is partly different from that of the first embodiment, but the other features are similar to those of the first embodiment. A description will therefore be given mainly of how the sixth embodiment differs from the first embodiment. As for the features common to the first embodiment, a description and illustration of them will be omitted.

The band member 44 includes a plurality of arch portions 51, a plurality of connection portions 52 connecting the arch portions 51, and a plurality of flat portions 62 provided for the respective arch portions 51. The arch portions 51 are arranged on the imaginary circle 46 on the outer tube 43 whose center is the same as the central axis C. The connection portions 52 extend in directions intersecting with the imaginary circle 46. The flat portions 62 are located at the apex positions of the arch portions 51 and extend substantially in parallel to the imaginary circle 46. As compared with the band members 44 of the foregoing embodiments, the band member 44 of the sixth embodiment enables a decrease in the widthwise dimension W as measured in the direction intersecting with the imaginary circle 46.

According to the sixth embodiment, the flat portions 62 are provided at the apex positions of the arch portions. With this structure, the installation space of the band member 44 can be small. This contributes to reduction of the size of the distal end structure of the insertion apparatus.

Seventh Embodiment

An endoscope apparatus 11 according to the seventh embodiment will be described with reference to FIG. 19. The endoscope apparatus 11 of the seventh embodiment differs from that of the first embodiment in terms of the material of the band member 44 and the position where the band member 44 is provided, but the other features are similar to those of the first embodiment, including the shape of the band member 44. A description will therefore be given mainly of how the sixth embodiment differs from the first embodiment. As for the features common to the first embodiment, a description and illustration of them will be omitted.

Figure 19:
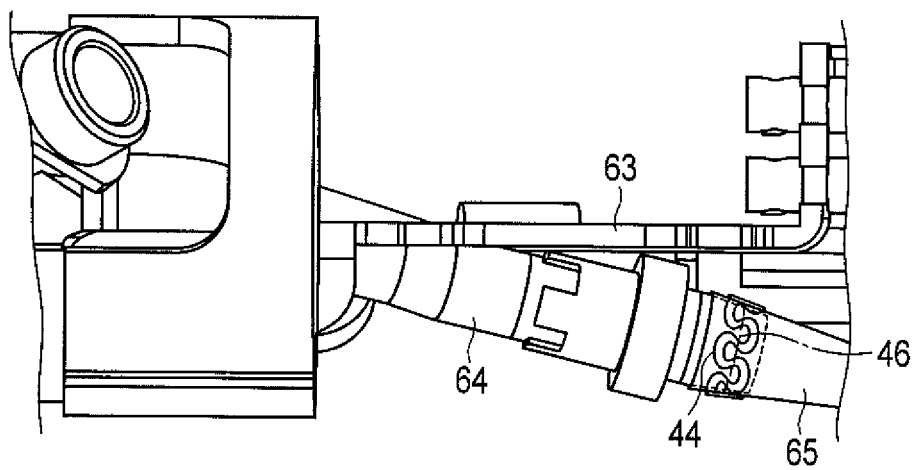
FIG. 19 is a perspective view showing a band member used inside the operation section of an endoscope apparatus according to the seventh embodiment.

As shown in FIG. 19, the operation section 25 comprises: a case 36 (see FIG. 1) formed, for example, of a synthetic resin; a frame 63 located in the frame 63; a metallic suction tube 64 secured to the frame 63; a resin tube 65 covering the circumference of the end of the suction tube 64 and connected to the suction tube 64; and a band member 44 which secures the tube 65 to the function tube 64. The suction tube 64 is an example of a linearly-extending tube.

The distal end of the suction tube 64 is connected to the nozzle 23 of a distal-end hard portion 21 through a connection tube. Tube 65 is a cylindrical member formed of a synthetic resin material or a thermoplastic elastomer such as PTFE and PFA. The tube 65 covers the end of the suction tube 64 and connected to the suction tube 64. The tube 65 is connected to an air supply/water supply/suction apparatus 15. Air and water can be supplied from the nozzle 23 of the distal-end hard portion 21, and a liquid, a tissue, etc. sucked through a treatment tool insertion channel 29 can be made to flow to the air supply/water supply/suction apparatus 15.

An insertion section 28 comprises a band member 44 arranged on the outer surface of an outer tube 43 and securing the outer tube 43 to be insertion section main body 41.

The band member 44 is provided on the outer tube 43 in such a manner as to meander on an imaginary circle 46 on the outer tube 43 whose center is the same as the central axis C of the insertion section main body 41. The band member 44 can be regarded as a repeated pattern of the letter "S". The band member 44 can fix the outer tube 43 to the distal-end hard portion 21 in a watertight manner. The band member 44 is made of a synthetic resin. To be more specific, the band member 44 is made of a fiber reinforced plastic (FRP), for example. Since the band member 44 is a repeated pattern of the letter "S", it can be expanded or contracted in the direction along the imaginary circle.

The band member 44 includes a plurality of arch portions 51 and a plurality of connection portions 52 connecting the arch portions 51. The arch portions 51 are arranged on the imaginary circle 46 on the outer tube 43 whose center is the same as the central axis C. Each of the arch portions 51 overlaps the adjacent arch portions 51 in the direction along the imaginary circle 46. The connection portions 52 extend in directions intersecting with the imaginary circle 46. As shown in FIG. 5, dimension A of the connection portion 52 (i.e., the dimension as measured in the transverse direction of the connection portion 52) is equal to or less than dimension B of the arch portion 51 (i.e., the dimension as measured in the transverse direction of the arch portion 51). That is, A≤B. In the seventh embodiment, an adhesive layer 45 for covering the band member 44 is not provided.

According to the seventh embodiment, the insertion apparatus comprises: a linearly-extending tubular member; a tube 65 covering the circumference of the tubular member; and an annular band member 44 covering the tube 65 and securing the tube 65 to the tubular member, the annular band member being provided in such a manner as to meander on an imaginary circle 46 on the tube whose center is the same as the central axis C of the tubular member, the annular band member being configured to shrink in a direction along the imaginary circle 46 and thereby secure the tube 65 to the tubular member.

With this structure, the tube 65 can be secured to the tubular member by a one-touch operation by covering the outer surface of the tube 65 with the annular band member 44 in the expanded state. Accordingly, an operator who secures the tube 65 does not require skill, and the assembling operation of the insertion apparatus can be simplified. In addition, the force with which to secure the tube 65 is prevented from being non-uniform.

Eighth Embodiment

Figure 20:
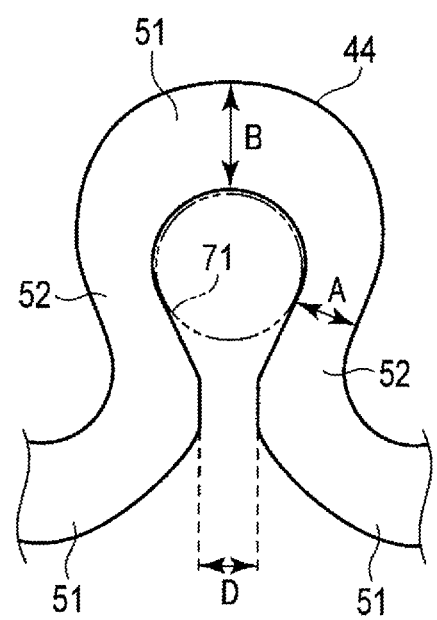
FIG. 20 is a front view showing part of a band member used for the insertion section of an endoscope apparatus according to the eighth embodiment.

An endoscope apparatus 11 according to the eighth embodiment will be described with reference to FIG. 20. The endoscope apparatus 11 of the eighth embodiment differs from that of the first embodiment in terms of the shape of a band member 44 employed, but the other features are similar to those of the first embodiment. A description will therefore be given mainly of how the eighth embodiment differs from the first embodiment. As for the features common to the first embodiment, a description and illustration of them will be omitted.

The band member 44 can fix the outer tube 43 to the distal-end hard portion 21 in a watertight manner. The band member 44 is made of a metallic material. To be more specific, the band member 44 is made of such a titanium-based alloy as a Ni—Ti alloy. Because of the property of the titanium-based alloy, the band member 44 can provide superelasticity. In the state where the band member covers the outer surface of the outer tube, the band member provides a watertight structure between the distal-end hard portion and the outer tube. In addition, the band member provides such a tightening force as prevents the outer tube from slipping off the distal-end hard portion. The band member 44 includes a plurality of arch portions 51 and a plurality of connection portions 52 connecting the arch portions 51. As shown in FIG. 3, the arch portions 51 are arranged on the imaginary circle 46 on the outer tube 43 whose center is the same as the central axis C of the insertion section main body 41. The connection portions 52 extend in directions intersecting with the imaginary circle 46. As shown in FIG. 20, dimension A of connection portion 52, which is the widthwise dimension of the connection portion 52 (i.e., the dimension as measured in the transverse direction of the connection portion 52), is equal to or less than dimension B of arch portion 51, which is the widthwise dimension of the arch portion 51 (i.e., the dimension as measured in the transverse direction of the arch portion 51). That is, A B.

The inward portion of each arch portion 51 has a shape that is along a circle 71 having a predetermined diameter. The outlines of the connection portions 52 are tangential lines of the circle 71. Gap D is provided between the adjacent arch portions 51.

In addition to the advantages of the first embodiment, the eighth embodiment has the advantage that the band member 44 is simple in shape and can be worked with ease. Accordingly, the working time can be shortened, and the manufacturing cost can be lowered.

The present invention is not limited to the above-described embodiments, and can be modified in various manners when reduced to practice, without departing from the gist of the invention. For example, a band member 44 such as that described in each embodiment or modification may be provided on an outer tube beforehand. In this case, the outer tube 43 integral with the band member 44 can be made by insert molding. In addition, the endoscope apparatuses 11 of the foregoing embodiments may be properly combined in such a manner as to construct one endoscope apparatus.

In connection with the embodiments, reference was made to the case where an endoscope is employed as an example of an insertion apparatus. Other examples of the insertion apparatus may include an apparatus that does not comprise an illumination optical system (including a light source and an illumination lens for a distal-end hard portion) or an observation optical system (including an image capturing apparatus, a monitor and an objective lens for a distal-end hard portion).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion apparatus comprising:
   an insertion section main body to be inserted into an examinee;
   a covering configured to cover an outer circumference of the insertion section main body; and
   a first annular band member provided on the outer circumference of the covering such that the first annular band member meanders in a direction along a circular outer circumferential line that is provided on the outer circumference of the covering and whose center corresponds to a central axis of the insertion section main body, the first annular band member being configured to shrink and thereby secure the covering to the insertion section main body, the first annular band member including:
   a plurality of arch portions arranged in a direction along the circular outer circumferential line, and
   a plurality of connection portions that connect the arch portions together.

2. The insertion apparatus according to claim 1, wherein the first annular band member is configured to shrink along the same plane as the circular outer circumferential line.

3. The insertion apparatus according to claim 2, further comprising:
   a second annular band member which is symmetric with the first annular band member with respect to a reference line parallel to the circular outer circumferential line and which is integral with the band member.

4. The insertion apparatus according to claim 2, further comprising:
   a second annular band member which meanders on the circular outer circumferential line at a pitch different from that of the first annular band member.

5. The insertion apparatus according to claim 1, wherein the arch portions has a widthwise dimension greater than a widthwise dimension of the connection portions.

6. The insertion apparatus according to claim 5, wherein each of the arch portions overlaps adjacent arch portions in a direction along the circular outer circumferential line.

7. The insertion apparatus according to claim 6, wherein the first annular band member has a diameter smaller than that of the covering and is expansible to have a diameter larger than that of the covering when the first annular band member is fitted around the covering.

8. The insertion apparatus according to claim 7, wherein the first annular band member is formed from one flat plane, and is changed into a cylindrical shape when the first annular band member is fitted around the covering.

9. The insertion apparatus according to claim 8, wherein the arch portions include:
   center-side arch portions located closer to the central axis than the circular outer circumferential line circle; and
   outer-side arch portions located outward of the circular outer circumferential line and having a dimension greater than that of the center-side arch portions, as measured along the direction of the circular outer circumferential line.

10. The insertion apparatus according to claim 5, wherein the first annular band member forms a sine curve.

11. The insertion apparatus according to claim 1, wherein the first annular band member is formed of a metal having super elasticity.

12. The insertion apparatus according to claim 1, wherein the connection portions are provided with slits extending in directions in which the connection portions extend.

13. The insertion apparatus according to claim 1, wherein the arch portions comprise a flat portion at apexes thereof.

14. The insertion apparatus according to claim 1, further comprising:
   an adhesive layer covering the first annular band member.

15. The insertion apparatus according to claim 1, wherein the first annular band member winds back and forth in a direction perpendicular to the circular outer circumferential line.

* * * * *